United States Patent [19]

Reinehr et al.

[11] 4,277,621
[45] Jul. 7, 1981

[54] SUBSTITUTED 11-AMINO-UNDECA-4,8-DIENAL AND 11-AMINO-UNDECANAL DERIVATIVES AND PROCESSES FOR THEIR PREPARATION

[75] Inventors: Dieter Reinehr, Kandern, Fed. Rep. of Germany; Josef Pfeifer, Therwil, Switzerland

[73] Assignee: Ciba-Geigy Corporation, Ardsley, N.Y.

[21] Appl. No.: 83,140

[22] Filed: Oct. 9, 1979

[30] Foreign Application Priority Data

Oct. 18, 1978 [CH] Switzerland ............... 10769/78

[51] Int. Cl.³ ............ C07C 109/14; C07C 109/16; C07C 131/00
[52] U.S. Cl. ............... 564/250; 564/251; 564/253; 564/265; 564/268
[58] Field of Search .......... 260/566 A, 566 B, 563 R; 564/250, 251, 253, 265, 268

[56] References Cited

U.S. PATENT DOCUMENTS

| | | |
|---|---|---|
| 2,319,848 | 5/1943 | Clark et al. |
| 3,597,400 | 8/1971 | Kashiro et al. ............ 260/30.8 R |
| 3,706,802 | 12/1972 | Arrigo ............ 260/566 F |
| 3,939,147 | 2/1976 | Hugelin et al. |

FOREIGN PATENT DOCUMENTS

| | | |
|---|---|---|
| 1720513 | 7/1971 | Fed. Rep. of Germany. |
| 2642244 | 3/1977 | Fed. Rep. of Germany. |
| 905475 | 9/1962 | United Kingdom. |
| 919096 | 2/1963 | United Kingdom. |

OTHER PUBLICATIONS

Hasek, Robert H. et al., *J. Org. Chem.*, vol. 22 (1961) pp. 1822–1825.

Reinehr, Dieter, *Helv. Chemica Acta*, vol. 61 (1978) pp. 1122–1124.
Wender, Paul A. et al., *J. Org. Chem.*, vol. 43 (1978) pp. 782–784.
Taylor, Grant K. et al., *Tetrahedron*, vol. 34 (1978) pp. 833–839.

*Primary Examiner*—Natalie Trousof
*Assistant Examiner*—L. Hendriksen
*Attorney, Agent, or Firm*—Luther A. R. Hall

[57] ABSTRACT

Novel substituted 11-amino-undeca-4,8-dienal and 11-amino-undecanal aldehyde-derivatives of the formulae Ia

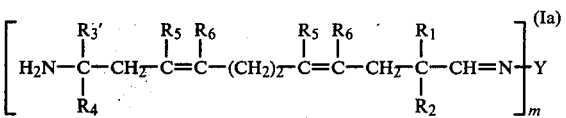

or Ib

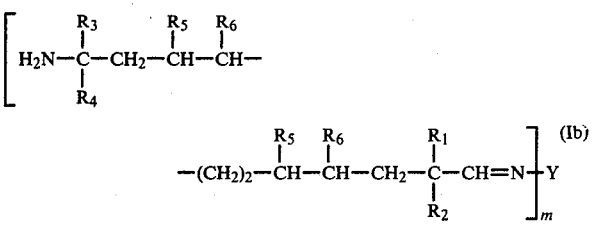

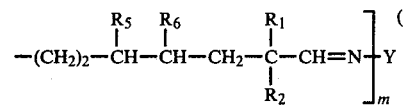

in which $R_1$ to $R_6$, Y and m are as defined in patent claim 1, and processes for their preparation are described. The compounds of the formulae Ia and Ib can be catalytically hydrogenated to novel 1,11-diaminoundecanes, which, in turn, can be used, for example, for the preparation of polycondensation products, in particular transparent polyamides, or as curing agents for epoxide resins.

9 Claims, No Drawings

SUBSTITUTED 11-AMINO-UNDECA-4,8-DIENAL AND 11-AMINO-UNDECANAL DERIVATIVES AND PROCESSES FOR THEIR PREPARATION

The present invention relates to novel substituted 11-amino-undeca-4,8-dienal and 11-amino-undecanal aldehyde-derivatives and processes for their preparation. The novel 11-amino-undeca-4,8-dienal and 11-amino-undecanal aldehyde-derivatives are valuable intermediates for the preparation of substituted 1,11-diaminoundecanes.

It is known that substituted or unsubstituted alkylenediamines are suitable for the preparation of transparent polyamides. Thus, for example, German Offenlegungsschrift No. 1,720,513 describes generically boil-resistant, transparent polyamides obtained from aromatic dicarboxylic acids and unsubstituted or alkyl-substituted alkylenediamines having 1–10 C atoms in the chain, which are substituted at least on one of the two terminal C atoms by an alkyl group having 1–4 C atoms. The concrete disclosure, however, is restricted to transparent polyamides obtained from aromatic dicarboxylic acids and alkylenediamines of the abovementioned type having not more than 7 C atoms in the chain. British Pat. Nos. 905,475 and 919,096 describe further transparent polyamides obtained from terephthalic acid, isophthalic acid or mixtures thereof and hexamethylenediamines with at least three C atoms, introduced by alkyl substitution, in one or more side chains, such as 2,2,4- and 2,4,4-trimethylhexamethylenediamine, 2-methyl-4-ethylhexamethylenediamine and 2-ethyl-4-methylhexamethylenediamine or mixtures of the isomers of such hexamethylenediamines. Alkylenediamines are also suitable as the co-condensation component for the preparation of transparent polyamides from 4,4′-diaminodicyclohexylalkanes and aromtic dicarboxylic acids and, if desired, further co-condensation components, such as aminocarboxylic acids or their lactams and aliphatic dicarboxylic acids. Polyamides of this type are described, for example, in U.S. Pat. No. 3,597,400 and in German Offenlegungsschrift No. 2,642,244. However, with regard to the absorption of water, the stability to hydrolysis, the heat distortion resistance and/or the dimensional stability under the action ·of moisture, these previously disclosed polyamides and copolyamides leave something to be desired, and, as a result of this, the mechanical and electrical properties of these polyamides are also impaired. Furthermore, some of the said polyamides are thermoplastically processable only with difficulty or are brittle products.

Novel substituted 11-amino-undeca-4,8-dienal and 11-amino-undecanal aldehyde-derivatives have now been found which can be converted to substituted 1,11-amino-undecanes, which, in turn, are suitable for the preparation of transparent polyamides which are free from the abovementioned disadvantages.

The novel substituted 11-amino-undeca-4,8-dienal and 11-amino-undecanal aldehyde-derivatives have the formulae Ia

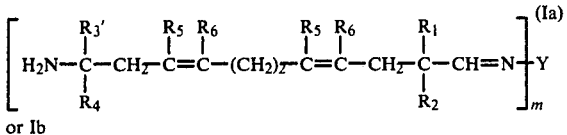

or Ib

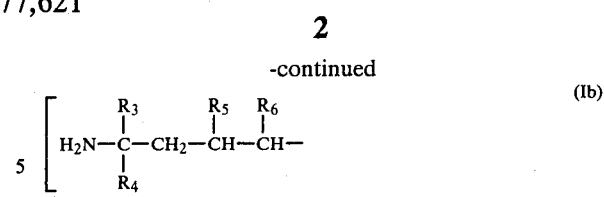

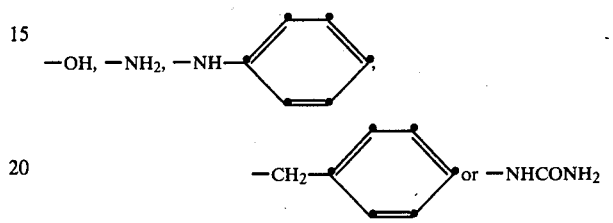

in which m is the number 1 or 2, Y is $-OH$, $-NH_2$, $-NH-\!\!\!\bigcirc$, $-CH_2-\!\!\!\bigcirc$ or $-NHCONH_2$ if m=1 and is a direct bond if m=2, $R_1$ is alkyl having 1–12 C atoms, $R_2$ is hydrogen or alkyl having 1–12 C atoms, $R_3$ is alkyl having 1–12 C atoms, cycloalkyl having 4–12 ring C atoms, aralkyl having 7 or 8 C atoms, substituted or unsubstituted aryl, pyridyl, furyl or thienyl, $R'_3$ has the meaning defined for $R_3$ or, if $R_4$ is hydrogen, is also $-CH\!=\!CH$-alkyl or $-C$(alkyl)$=CH$-alkyl, each having 1–4 C atoms in the alkyl moiety, and $R_4$ is hydrogen, alkyl having 1–12 C atoms, cycloalkyl having 4–12 ring C atoms, aralkyl having 7 or 8 C atoms or substituted or unsubstituted aryl, or $R_1$ and $R_2$ and/or $R_3$ and $R_4$, or $R_3'$ and $R_4$, together are alkylene having 3–11 C atoms, and $R_5$ and $R_6$ independently of one another are hydrogen or methyl.

Alkyl groups $R_1$ to $R_4$ can be straight-chain or branched. Alkyl groups $R_1$, $R_2$ and $R_4$ preferably have 1–5 C atoms and are straight-chain. Alkyl groups $R_3$ or $R_3'$ advantageously have 1–7 C atoms; branched alkyl groups $R_3$ and $R_3'$ having 1–7 C atoms are particularly preferred. Examples of alkyl groups $R_1$ to $R_4$ are: the methyl, ethyl, n-propyl, isopropyl, n-, sec.- and tert.-butyl, n-pentyl, 2- or 3-pentyl, n-hexyl, 2- or 3-heptyl, n-octyl, n-decyl and n-dodecyl groups.

The alkyl moieties in a $-CH\!=\!CH$-alkyl or $-C$(alkyl)$=CH$-alkyl group $R_3'$ are preferably straight-chain and in particular are methyl or ethyl.

Cycloalkyl groups $R_3$, $R_3'$ and $R_4$ can be unsubstituted or substituted by $C_{1-4}$-alkyl groups. In particular they are cycloalkyl substituted by a methyl or ethyl group.

Preferably, however, cycloalkyl groups $R_3$, $R_3'$ and $R_4$ are unsubstituted and have 5–8 ring C atoms. The cyclopentyl group and in particular the cyclohexyl group are particularly preferred.

Aralkyl groups $R_3$, $R_3'$ and $R_4$ are in particular the benzyl, methylbenzyl or phenylethyl group. Suitable substituents in substituted aryl $R_3$, $R_3'$ or $R_4$ are, in particular, alkyl groups having 1–4 and especialy 1 or 2 C atoms. Aryl groups $R_3$, $R_3'$ and $R_4$ can carry several alkyl groups but preferably are substituted only by one alkyl group. Particularly preferred aryl groups are the 1- or 2-naphthyl group, phenyl substituted by an alkyl group having 1–4 and especially 1 or 2 C atoms and, very particularly, unsubstituted phenyl.

Pyridyl, furyl or thienyl groups $R_3$ or $R_3'$ are in particular the 3-pyridyl, 4-pyridyl, 2-furyl and 2-thienyl groups.

Alkylene groups formed by $R_1$ and $R_2$ and/or $R_3$ and $R_4$, or $R_3'$ and $R_4$, together preferably have 4–7 C atoms. In particular such groups are the tetramethylene group and very particularly the pentamethylene group.

Preferred compounds of the formulae Ia and Ib are those in which $R_1$ is alkyl having 1–5 C atoms and $R_2$ is hydrogen or alkyl having 1–5 C atoms, or $R_1$ and $R_2$ together are alkylene having 4–7 C atoms, $R_3$ is alkyl having 1–7 C atoms, cycloalkyl having 5–8 C atoms or unsubstituted phenyl, $R_3'$ has the meaning defined for $R_3$ or, if $R_4$=H, is also $-C(C_2H_5)=CH-CH_3$, $R_4$ is hydrogen or alkyl having 1–5 C atoms and $R_5$ and $R_6$ are each hydrogen.

Particularly preferred compounds of the formulae Ia and Ib are those in which m is the number 1, Y is —OH, $R_1$ is alkyl having 1–5 C atoms and $R_2$ is alkyl having 1–5 C atoms or hydrogen, or $R_1$ and $R_2$ together are alkylene having 4–7 C atoms, $R_3$ is branched alkyl having 3–7 C atoms or cycloalkyl having 5–8 C atoms, $R_3'$ has the meaning defined for $R_3$ or is $-C(C_2H_{5L})=CH-CH_3$ and $R_4$, $R_5$ and $R_6$ are each hydrogen. Very particularly preferred compounds of the formulae Ia and Ib are those in which m is the number 1, Y is —OH, $R_1$ and $R_2$ are each methyl or ethyl or together are $C_{4-7}$-alkylene, especially pentamethylene, $R_3$ and $R_3'$ are isopropyl, 3-pentyl or $C_{5-8}$-cycloalkyl, especially cyclohexyl, and $R_4$, $R_5$ and $R_6$ are each hydrogen.

The compounds of the formulae Ia and Ib can be prepared by (A) reacting a compound of the formula II

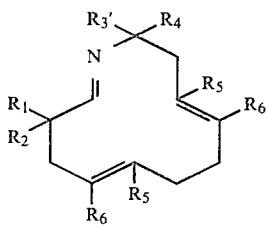
(II)

with a compound of the formula IIIa or IIIb

 (IIIa)

or

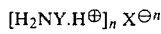 (IIIb)

to give a compound of the formula Ia, or (B) catalytically hydrogenating a compound of the formula II to a compound of the formula IV

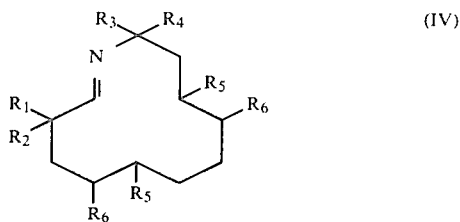
(IV)

and reacting the compound of the formula IV with a compound of the formula IIIa or IIIb to give a compound of the formula Ib. In the above formulae II, IIIa, IIIb and IV, $R_1$ to $R_6$ are as defined under formula Ia and/or Ib, Y is as defined in the formulae Ia and Ib but is not a direct bond, X is the anion of an inorganic acid which is non-oxidising under the reaction conditions and n is an integer corresponding to the valency of X.

Compounds of the formula Ib can also be obtained by catalytic hydrogenation of compounds of the formula Ia. However, the preparation of compounds of the formula Ib by the process described under (B) is preferred.

The reaction of the 1-aza-1,5,9-cyclododecatrienes of the formula II and the 1-aza-cyclododecenes of the formula IV is advantageously carried out in an aqueous medium at temperatures of between about 20° and 100° C. X is, for example, the anion of hydrochloric or hydrobromic acid or of sulfuric or phosphoric acid. Examples of compounds of the formula IIIa or IIIb which are used are phenylhydrazine, benzylamine or the corresonding hydrochlorides or hydrobromides, hydroxylamine hydrochloride, hydroxylamine sulfate, hydroxylamine hydrogen sulfate, semicarbazide hydrochloride, hydrazine sulfate and hydrazine monohydrobromide or monohydrochloride. The compound of the formula IIIa in which Y=—$NH_2$ is preferably employed in the form of the hydrate.

The compounds of the formulae II and IV are advantageously employed in an essentially stoichiometric amount, based on the compound of the formula IIIa or IIIb. Advantageously, however, a slight excess of the compound of the formula IIIa or IIIb is used. If the compounds of the formula II or IV and the compounds of the formula IIIa or IIIb in which Y=—$NH_2$ are employed in a molar ratio of about 1:1, compounds of the formula Ia or Ib are obtained in which m=1 and Y=—$NH_2$. When the molar ratio of the compound of the formula II or IV to the compound of the formula IIIa or IIIb in which Y=—$NH_2$ is at least 2:1, on the other hand, compounds of the formula Ia or Ib are formed in which m=2 and Y is a direct bond.

In the course of the above reactions, compounds of the formulae Va or Vb

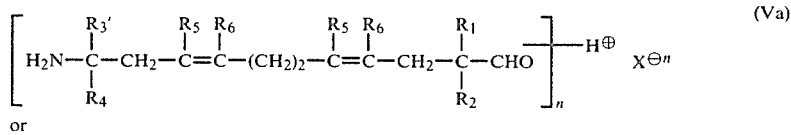
(Va)

or

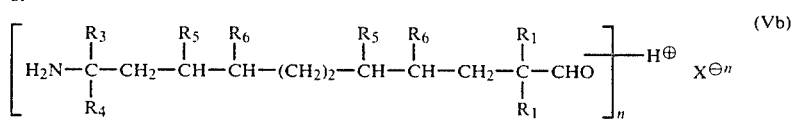
(Vb)

in which $R_1$ to $R_6$, X and n are as defined above, can form as intermediates.

In general, it is advisable to carry out the reaction with the addition of an inorganic acid which is non-oxidising under the reaction conditions, such as dilute HCl or sulfuric acid, especially when compounds of the formula IIIa are used.

After the reaction has ended, the reaction mixture is advantageously neutralised by the addition of a suitable organic or inorganic base, such as alkali metal hydroxides, carbonates or bicarbonates or alkaline earth metal hydroxides, carbonates or bicarbonates, or tertiary amines, for example triethylamine or pyridine. The base used is preferably an alkali metal hydroxide, especially sodium hydroxide or potassium hydroxide.

The catalytic hydrogenation of the 1-aza-1,5,9-cyclododecatrienes of the formula II to 1-aza-cyclodecenes of the formula IV and also the catalytic hydrogenation of 11-amino-undeca-4,8-dienal aldehyde-derivatives of the formula Ia to 11-amino-undecanal aldehyde-derivatives of the formula Ib can be carried out by methods known per se, in the presence of a suitable inert organic solvent, such as aliphatic or cycloaliphatic hydrocarbons, for example n-pentane, n-hexane, cyclopentane or cyclohexane, or cyclic ethers, for example tetrahydrofuran, tetrahydropyran or dioxan. Preferred solvents are cyclohexane and tetrahydrofuran. The catalysts used are advantageously noble metal catalysts, such as platinum, rhodium, palladium and ruthenium catalysts. Rhodium/aluminium oxide and palladium/charcoal catalysts are preferred. In general, the hydrogenation is carried out in a closed system under a pressure of about 1–200 bars and especially of 1–130 bars and at temperatures of between about 0° and 150° C. and in particular of between about 25° and 100° C.

The starting materials of the formulae IIIa and IIIb are known. The compounds of the formula II can be prepared in a manner analogous to that described in Helv. Chim. Acta, 61, Fasc. 3, 1122–1124 (1978), by nickel-catalysed co-oligomerisation of 2-aza-1,3-butadienes of the formula VI

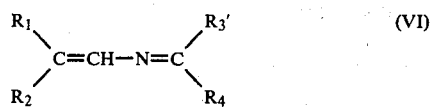

with compounds of the formula VII

in which formulae $R_1$ to $R_6$ are as defined under the formulae Ia and Ib. Suitable catalyst systems are described, for example, in German Offenlegungsschrift No. 2,330,087. Preferred catalysts are those which are obtained in situ by reduction of a nickel compound which is free from carbon monoxide, such as nickel stearate and in particular nickel acetylacetonate, with halogen-free metal-aryls or metal-alkyls, for example ethoxydiethylaluminium, in the presence of an alkyl- or aryl-phosphine or in the presence of an alkyl phosphite or aryl phosphite.

The above reaction is advantageously carried out in the presence of an inert organic solvent, such as n-hexane, n-heptane, benzene, toluene, diethyl ether or dioxan, at temperatures of between about −40° C. and +150° C.

The 2-aza-1,3-butadienes of the formula VI are known in most cases or can be prepared, for example, as follows: by reacting aldehydes $R_3'$-CHO or ketones

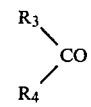

with alkenylamines

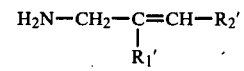

[$R_1'$=H or C 1–12 alkyl and $R_2'$=H or C 1–11 alkyl] or benzylamine, in which latter case $R_3'$ must be a —C(alkyl)=CH-alkyl or —CH=C_4-alkyl group, and subsequently isomerising the resulting compounds in the presence of catalysts, such as $K_2O/Al_2O_3$ catalysts, alkali metal alcoholates or alkaline earth metal alcoholates [cf., for example, B. A. Kazanskii et al., Zhurnal Organicheskoi Khimii, 6, No. 11, 2197–99 (1970); Izv. Akad. Nauk SSSR, Ser. Khim., No. 9, 2038–2045 (1975), Tetrahedron, 34, 833–839 (1978) and J. Org. Chem. 43, 782–784 (1978)], or by reacting allylamine or methallylamine with aldehydes $(R_1)(R_2'')$—CH—CHO [$R_2''$ as $R_2$, but not H] and subsequently isomerising the resulting compounds $(R_1)(R_2'')$—CH—CH=N-CH_2—C(R)=CH_2 [R=H or methyl] in the presence of catalysts, such as potassium tert.-butylate, or by reacting aldehydes $R_1$—CH($R_2''$)-CHO [$R_2''$ same as $R_2$, but not H] with ammonia (cf., for example, U.S. Pat. No. 2,319,848) and, if appropriate, further reacting the compounds

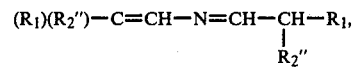

thus obtained, with suitable ketones or aldehydes (cf., example, U.S. Pat. No. 3,706,802).

The compounds of the formulae Ia and Ib can be converted by means of catalytic hydrogenation to novel diamines of the formula VIII

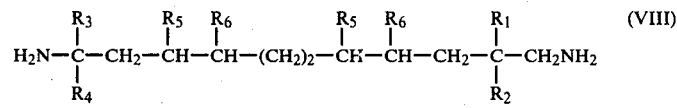

in which $R_1$ to $R_6$ are as defined under formulae Ia and Ib. The hydrogenation is advantageously carried out in a closed system under 1–200 bars and in particular 1–130 bars, and in the presence of an inert organic solvent, such as methanol, ethanol, propanol or isopropanol, and if desired in the presence of liquid ammonia or sodium hydroxide. The catalysts used are preferably nickel catalysts, especially Raney nickel.

The diamines of the formula VIII are suitable, for example, in the preparation of polycondensation products, in particular polyamides, or as curing agents for epoxide resins. Transparent polyamides, which can be obtained by polycondenation of diamines of the formula I, in which $R_3$ is not a heterocyclic radical, with aromatic dicarboxylic acids, in particular terephthalic acid and/or isophthalic acid, and, if desired, further long-chain diamines and aliphatic dicarboxylic acids, are distinguished by high glass transition temperatures and, accordingly, high distortion resistance, good thermoplastic processability, for example by the injection moulding or extrusion process, low absorption of water, coupled with a reduced dependence of the mechanical and electrical properties on the atmospheric humidity, improved stability to hydrolysis and also stability to boiling water.

EXAMPLE 1

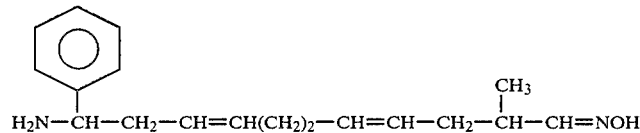

(a) 7.7 g (0.03 mol) of nickel acetylacetonate and 7.85 g (0.03 mol) of tripheyl phosphine are dissolved under argon in 200 g of absolute toluene, after which the solution is saturated at 20°–25° C. with 1,3-butadiene. 10.2 g (0.09 mol) of ethoxy-diethyl-aluminium are then added slowly dropwise, whilst passing a gentle stream of 1,3-butadiene into the solution. The reaction mixture is heated to 70° C. and, whilst passing in a vigorous stream of 1,3-butadiene, 495 g (3.41 mols) of N-benzylidene-propenylamine are added dropwise in the course of 1 hour at such a rate that the butadiene passed in is just consumed. The reaction mixture is stirred for a further 1 hour at 70° C., during which time 1,3-butadiene is continuously passed in, and is then cooled to 20°–25° C. In order to inactivate the catalyst, 0.96 g (0.03 mol) of sulfur is added to the reaction solution and the solution is distilled. This yields 750 g (2.97 mols) of 3-methyl-12-phenyl-1-aza-1,5,9-cyclododecatriene in the form of a mixture of the cis and trans isomers (cis: trans=65:35); boiling point 112°–113° C./1 Pa; $n_D^{20} = 1.5505$; melting point (cis isomer) = 57°–58° C.

(b) 502 g (1.98 mols) of 3-methyl-12-phenyl-1-aza-1,5,9-cyclododecatriene are added dropwise in the course of 1.5 hours to 220 g of 37% hydrochloric acid at a rate such that the temperature does not rise above 80° C. The mixture is then cooled to room temperature (20°–25° C.) and 140 g (2.02 mols) of hydroxylamine hydrochloride are added. About 185 g (4.6 mols) of solid sodium hydroxide are added in the course of one hour, the mixture being cooled with a waterbath, until the pH of the aqueous solution is 10–11. The organic phase which separates out is separated off and washed with water until neutral. 567 g (1.98 mols) of 2-methyl-11-phenyl-11-amino-undeca-4,8-dienal oxime are obtained in the form of a highly viscous liquid; yield 100% of theory.

Analysis for $C_{18}H_{26}N_2O$ (molecular weight 286.42): calculated C: 75.48%; H: 9.15%; N: 9.78%; O: 5.59%; found C: 76.00%; H: 9.33%; N: 9.28%; O: 5.20%.

Mass spectrum: molecule peak 286, fragment masses 269, 254, 214, 148, 121 and 106.

EXAMPLE 2

(a) 253 g (1 mol) of 3-methyl-12-phenyl-1-aza-1,5,9-cyclododecatriene are dissolved in 2 liters of cyclohexane and hydrogenated at 20°–25° C. and under an initial pressure of 100 bars in the presence of 40 g of rhodium-/aluminium oxide for 4 hours in a steel autoclave. After distilling off the solvent, 242 g (0.94 mol) of 3-methyl-12-phenyl-1-aza-cyclododecene are obtained as the main fraction, in the form of a mixture of the cis and trans isomers; boiling point 112° C./4 Pa. Mass spectrum: molecule peak 257, fragment masses 242, 172, 146, 117 and 104.

(b)

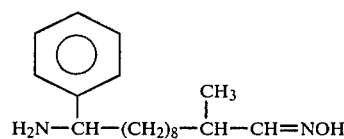

The procedure described in Example (1b) is repreated except that 146 g (0.568 mol) of 3-methyl-12-phenyl-1-azacyclododecene, 47 g (0.2875 mol) of hydroxylamine sulfate, 60 g (0.61 mol) of sulfuric acid and 200 ml of water are used. After working up as described in Example 1b), 165 g (0.567 mol) of 2-methyl-11-phenyl-11-amino-undecanal oxime are obtained in the form of a highly viscous liquid; yield 99.8% of theory.

Analysis for $C_{18}H_{30}N_2O$ (molecular weight 290.45): calculated C: 74.44%; H: 10.41%; N: 9.64%; O: 5.51%; found C: 74.9%; H: 10.1%; N: 9.1%; O: 5.2%.

Mass spectrum: molecule peak 290, fragment masses 273, 259, 216, 174, 146 and 106.

EXAMPLE 3:

(a) The procedure described in Example (1a) is repeated, except that 48.5 g (0.437 mol) of N-propylidene(2-methyl-propenylamine) [1-ethyl-4,4-dimethyl-2-aza-1,3-butadiene] and 61.0 g (1.13 mols) of 1,3-butadiene are used. Distillation yields 62.0 g (0.283 mol) of 3,3-dimethyl-12-ethyl-1-aza-1,5,9-cyclododecatriene; boiling point 65°–66° C./0.7 Pa; $n_D^{20} = 1.4864$.

The N-propylidene-(2-methylpropenylamine) was prepared as follows: 25 g (0.223 mol) of potassium tert-.butylate are suspended in one liter of anhydrous diethyl ether. 921 g (8.3 mols) of isobutylidene-allylamine are then added dropwise in the course of 1 hour, with continuous stirring, at a rate such that the temperature of the reaction mixture does not rise above 20° C. After the dropwise addition is ended, the reaction mixture is stirred for a further 5 hours at 20°–22° C. The reaction is then discontinued and the solvent is distilled over at a bath temperature of 40° C./27,000–35,000 Pa. The residue is distilled at a bath temperature of 70° C./13 Pa into a receiver cooled with $CO_2$/methanol. Subsequent fine distillation yields 808 g (7.93 mols) of N-propylidene-(2-methyl-propenylamine); boiling point 122° C.; $n_D^{20} = 1.471$.

(b) The procedure described in Example (1b) is repeated, except that 219 g (1 mol) of 3,3-dimethyl-12-ethyl-1-aza-1,5,9-cyclododecatriene, 147 g (1.5 mols) of sulfuric acid and 82 g (0.5 mol) of hydroxylamine sulfate are used. Working up yields 222 g (0.879 mol) of 2,2-dimethyl-11-ethyl-amino-undeca-4,8-dienal oxime in the form of a highly viscous liquid; yield 87.9% of theory; boiling point 162°14 164° C./7 Pa.

Analysis for $C_{15}H_{28}N_2O$ (molecular weight 252.40): calculated C: 71.38%; H: 11.18%; N: 11.10%; O: 6.34%; found C: 71.07%; H: 11.33%; N: 10.97%; O: 6.59%.

Mass spectrum: molecule peak 252, fragment masses 223, 208, 166, 140 and 58. $^1$H-NMR spectrum $\tau$ (ppm): 2.72 (s), 4.58 (m), 5–7 (m) 7.31 (quin), 7.87 (m), 8.4–8.8 (m), 8.90 (s) and 9.05 (t) in a ratio of 1:4:1:1:8:2:11.

EXAMPLE 4

(a) The procedure described in Example (2a) is repeated, except that 438 g (2 mols) of 3,3-dimethyl-12-ethyl-1-aza-1,5,9-cyclododecatriene are used. Distillation yields 412 g (1.85 mols) of 3,3-dimethyl-12-ethyl-1-azacyclododecene; boiling point 61°–63° C./4 Pa; $n_D^{20}=1.4721$. Mass spectrum: molecule peak 223, fragment masses 194, 138, 124 and 112. $^1$H-NMR spectrum $\tau$ (ppm): 2.53 (s), 7.22 (m), 8.2–8.8 (m), 8.87 (s), 8.91 (s) and 9.19 (t) in a ratio of 1:1:18:6:3.

(b) The procedure described in Example (1b) is repeated, except that 223 g (1 mol) of 3,3-dimethyl-12-ethyl-1-azacyclododecene, 82 g (0.5 mol) of hydroxylamine sulfate, 150 g of sulfuric acid and 400 ml of water are used. Distillation yields 245 g (0.955 mol) of 2,2-dimethyl-11-ethyl-11-amino-undecanal oxime; yield 95.5% of theory; boiling point 155°–160° C./7 Pa.

Analysis for $C_{15}H_{32}N_2O$ (molecular weight 256.43): calculated C: 70.26%; H: 12.58%; N: 10.93%; O: 6.24%; found C: 70.60%; H: 12.28%; N: 11.00%; O: 6.53%.

Mass spectrum: molecule peak 256, fragment masses 239, 227, 184, 170, 140 and 58.

$^1$H-NMR spectrum $\tau$ (ppm): 2.74(s), 5.6–6.5(m), 7.35(m), 8.4–8.8(m), 8.91(s) and 9.07(t) in a ratio of 1:1:1:20:6:3.

EXAMPLE 5

(a) Analogously to Example (1a), 122.5 g (0.98 mol) of N-isobutylidene-2-methylpropenylamine [prepared by reacting isobutyraldehyde with ammonia in accordance with J. Org. Chem., 26, 1822–25 (1961)] are reacted with 1,3-butadiene. Distillation yields 212.5 g (0.912 mol) of 3,3-dimethyl-12-isopropyl-1-aza-1,5,9-cyclododecatriene; boiling point 54°–55° C./1.33 Pa; $n_D^{20}=1.4832$.

(b) The procedure described in Example (1b) is repeated, except that 233.4 g (1 mol) of 3,3-dimethyl-12-isopropyl-1-aza-1,5,9-cyclododecatriene, 100 g of 37% hydrochloric acid, 200 ml of water and 69.5 g (1.0 mol) of hydroxylamine hydrochloride are used. Working up and subsequent distillation yields 245 g (0,92 mol) of 2,2-dimethyl-11-isopropyl-11-amino-undeca-4,8-dienal oxime; yield 92% of theory; boiling point 158°–162° C./4 Pa; $n_D^{20}=1.4930$.

Analysis for $C_{16}H_{30}N_2O$ (molecular weight 266.43): calculated C: 72.13%; H: 11.35%; N: 10.52%; O: 6.01%; found C: 72.86%; H: 11.39%; N: 10.21%; O: 5.65%. Mass spectrum: molecule peak 266, fragment masses 261, 223, 164, 140 and 72.

$^1$H-NMR spectrum $\tau$ (ppm): 2.73(s), 4.6(m), 5–7(m), 7.35–7.55(m), 7.89(m), 8.2–8.6(m), 8.90(s) and 9.05(d) in a ratio of 1:4:1:1:8:1:14.

EXAMPLE 6

The procedure described in Example (5b) is repeated, except that 300 ml of water are used in place of 110 g of 37% hydrochloric acid and 200 ml of water. After a reaction time of 45 minutes at 100° C. and working up as described in (5b), 2,2-dimethyl-11-isopropyl-11-amino-un deca-4,8-dienal oxime is obtained in a yield of 93% of theory.

EXAMPLE 7

(a) The procedure described in Example (2a) is repeated, except that 466.8 g (2 mols) of 3,3-dimethyl-12-isopropyl-1-aza-1,5,9-cyclododecatriene are used. Distillation yields 425 g (1.79 mols) of 3,3-dimethyl-12-isopropyl-1-aza-cyclododecene; boiling point 92°–94° C./4 Pa; $n_D^{20}=1.4706$. Mass spectrum: molecule peak 237, fragment masses 212, 194, 138 and 126.

$^1$H-NMR spectrum $\tau$ (ppm): 2.59(s), 7.51(m), 8.1–8.8(m), 8.87(s), 8.90(s) and 9.12(dd) in a ratio of 1:1:17:6:6.

(b) The procedure described in Example (1b) is repeated, except that 118.7 g (0.5 mol) of 3,3-dimethyl-12-isopropyl-1-aza-cyclododecene, 35 g (0.5 mol) of hydroxylamine hydrochloride, 55 g of 37% hydrochloric acid, 200 ml of water and 50 g (1.25 mols) of solid sodium hydroxide are used. Distillation yields 127 g (0.47 mol) of 2,2-dimethyl-11-isopropyl-11-amino-undecanal oxime; yield 94% of theory; boiling point 145° C./4 Pa; $n_D^{20}=1.4761$.

Analysis for $C_{16}H_{34}N_2O$ (molecular weight 270.46): calculated C: 71.06%; H: 12.67%; N: 10.36%; O: 5.91%; found C: 71.13%; H: 12.68%; N: 10.30%; O: 5.91%. Mass spectrum: molecule peak 270, fragment masses 253, 236, 227, 209, 182 and 109.

$^1$H-NMR spectrum $\tau$ (ppm): 2.62(s), 5.6–6.5(m), 7.38(m), 8.1–8.75(m), 8.84(s) and 9.03(dd) in a ratio of 1:1:1:19:6:6.

EXAMPLE 8

(a) The procedure described in Example (1a) is repeated, except that 110 g (1.13 mols) of N-isopropylidene-propenylamine [prepared by reaction of acetone with allylamine and subsequent isomerisation; cf. Zhurnal Organicheskoi Khimii, 6, No. 11, 2197–9 (1970)] and 108 g (2 mols) of 1,3-butadiene are used. Distillation yields 187.0 g (0.91 mol) of 3,12,12-trimethyl-1-aza-1,5,9-cyclododecatriene; boiling point 55° C./4 Pa; $n_D^{20}=1.4985$.

(b) The procedure described in Example (1b) is repeated, except that 205 g (1 mol) of 3,12,12-trimethyl-1-aza-1,5,9-cyclododecatriene, 82 g (0.5 mol) of hydroxylamine sulfate, 110 g of sulfuric acid and 300 ml of water are used. Working up and subsequent distillation yield 205 g (0.86 mol) of 2,11,11-trimethyl-11-amino-undeca-4,8-dienal oxime; yield 86% of theory; boiling point 155° C./20 Pa; $n_D^{20}=1.4950$.

Analysis for $C_{14}H_{26}N_2O$ (molecular weight 238.38): calculated C: 70.54%; H: 11.00%; N: 11.75%; O: 6.71%; found C: 70.69%; H: 11.12%; N: 11.72%; O: 6.74%. Mass spectrum: molecule peak 238, fragment masses 223, 204, 190, 166, 126 and 58.

$^1$H-NMR spectrum $\tau$ (ppm): 2.75 (d), 4.58 (m), 5–7(m), 7.58 (quin), 7.9(m), 8.87(s) and 8.95(d) in a ratio of 1:4:1:1:10:9.

EXAMPLE 9

(a) The procedure described in Example (1a) is repeated, except that 678 g (3.31 mols) of N-cyclohexyl-methylidene-(cyclohexylidene-methylamine) [prepared by reacting cyclohexanecarbaldehyde with ammonia; boiling point 83° C./4 Pa; $n_D^{20}$ 1.5260] are used. Distillation 3,3-pentamethylene-hexyl-1-aza-1,5,9-cyclododecatriene; boiling point 140° C./3 Pa; $n_D^{20} = 1.5191$.

(b) The procedure described in Example (2a) is repeated, 3,3-pentamethylene-cyclohexyl-1-aza-1,5,9-cyclododecatriene are used. Distillation yields 733.9 g (2.32 mols) of 3,3-pentamethylene-12-cyclohexyl-1-aza-cyclododecene; yield 96.6% of theory; boiling point 140°–142° C./3 Pa; $n_D^{20} = 1.4982$. Mass spectrum: molecule peak 317, fragment masses 234, 206 and 138.

$^1$H-NMR spectrum $\tau$ (ppm): 2.72(s), 7.5(m) and 8.0–9.0(m) in a ratio of 1:1:37.

(c) The procedure described in Example (1b) is repeated, except that 317 g (1 mol) of 3,3-pentamethylene-12-cyclohexyl-1-aza-cyclododecene, 70 g (1 mol) of hydroxylamine hydrochloride, 100 g of 37% hydrochloric acid, 300 ml of water and 100 g of solid sodium hydroxide are used. The organic phase which separates out contains 340 g (0.97 mol) of 2,2-pentamethylene-11-cyclohexyl-11-amino-undecanal oxime; yield 97% of theory.

EXAMPLE 10

(a) The procedure described in Example (1a) is repeated, except that 1,010 g (6.35 mols) of N-benzylidene-(2-methyl-propenylamine) [prepared by reaction of benzaldehyde with methallylamine and subsequent isomerisation in the presence of potassium tert.-butylate; boiling point 65°–66° C./7 Pa; $N_D^{20} = 1.5836$] are used. After a reaction time of 2 hours at 85° C. and subsequent distillation, 1,398 g (5.24 mols) of 3,3-dimethyl-12-phenyl-1-aza-1,5,9-cyclododecatriene are obtained; boiling point 128°–130° C./4 Pa; melting point 66°–68° C.

(b) The procedure described in Example (1b) is repeated, except that 289.3 g (1.09 mols) of 3,3-dimethyl-12-phenyl-1-aza-1,5,9-cyclododecatriene, 88.7 g (0.54 mol) of hydroxylamine sulfate, 100 g of 37% hydrochloric acid, 400 ml of water and 100 g of solid sodium hydroxide are used. The organic phase which separates out contains 320 g (1.065 mols) of 2,2-dimethyl-11-phenyl-11-amino-undeca-4,8-dienal oxime; yield 97.9% of theory.

EXAMPLE 11

(a) The procedure described in Example (1a) is repeated, except that 273 g (2.02 mols) of N-2-furylidene-propenylamine [prepared by reaction of 2-furylaldehyde with allylamine and subsequent isomerisation in the presence of potassium tert.-butylate; boiling point 60°–62° C./67 Pa; $n_D^{20} = 1.6004$] are used. Distillation yields 210 g (0.865 mol) of 3-methyl-12-(2-furyl)-1-aza-1,5,9-cyclododecatriene; boiling point 106°–108° C./4 Pa; $n_D^{20} = 1.5260$.

(b) The procedure described in Example (1b) is repeated, except that 190 g (0.78 mol) of 3-methyl-12-(2-furyl)-1-aza-1,5,9-cyclododecatriene, 54 g (0.78 mol) of hydroxylamine hydrochloride, 84 g of sulfuric acid, 300 ml of water and 65 g of solid sodium hydroxide are used. The organic phase which separates out contains 201 g (0.728 mol) of 2-methyl-11-(2-furyl)-11-amino-undeca-4,8-dienal oxime; yield 93% of theory; $n_D^{20} = 1.5305$.

Analysis for $C_{16}H_{24}N_2O_2$ (molecular weight 276.38): calculated C: 69.53%; H: 8.75%; N: 10.14 %; O: 11.58%); found C: 71.00%; H: 8.73%; N: 9.11%; O: 11.18%.

Mass spectrum: molecule peak 276, fragment masses 259, 242, 228, 204, 148, 133 and 96.

$^1$H-NMR spectrum $\tau$ (ppm): 2.7–2.9(m), 3.7–3.9(m), 4.6(m), 6.03(t), 7.4–8.0(m) and 9.0(dd) in a ratio of 2:2:4:1:12:3.

EXAMPLE 12

(a) The procedure described in Example (1a) is repeated, except that 629 g (3.55 mols) of N-cyclopentyl-methylidene-(cyclopentylidenemethylamine) [prepared by reacting cyclopentanecarbaldehyde with ammonia; boiling point 125° C./1.86 × 10$^3$ Pa; $n_D^{20} = 1.5245$] are used. Distillation yields 798 g (2.8 mols) of 3,3-tetramethylene-12-cyclopentyl-1-aza-1,5,9-cyclododecatriene; boiling point 120° C./1 Pa.

(b) The procedure described in Example (2a) is repeated, except that 500 g (1.75 mols) of 3,3-tetramethylene-12-cyclopentyl-1-aza-1,5,9-cyclododecatriene are used. Distillation yields 470 g (1.63 mols) of 3,3-tetramethylene-12-cyclopentyl-1-aza-cyclododecene; yield 93% of theory; boiling point 130° C./7 Pa. Mass spectrum: molecule peak 289, fragment masses 220, 178, 142 and 98.

(c) The procedure described in Example (2b) is repeated, except that 470 g (1.63 mols) of 3,3-tetramethylene-12-cyclopentyl-1-aza-cyclododecane, 133 g (0.81 mol) of hydroxylamine sulfate and 162 g of 37% hydrochloric acid and also 400 ml of water are used. After neutralisation with solid sodium hydroxide, 525 g (1.63 mols) of 2,2-tetramethylene-11-cyclopentyl-11-amino-undecanal oxime are obtained; yield 100% of theory.

EXAMPLE 13

(a) 710 g (3.93 mols) of N-2-methyl-pentylidene-(2-methyl-penten-1-yl-amine) [prepared by reacting 2-methyl-valeraldehyde with ammonia in accordance with U.S. Pat. No. 2,319,848] and 432 g (8.0 mols) of 1,3-butadiene are reacted by a procedure analogous to that described in the preceding examples. After working up the reaction mixture, 995 g (3.45 mols) of 3-methyl-3-n-propyl-12-(2-pentyl)-1-aza-1,5,9-cyclododecatriene are obtained in the form of a mixture of isomers (2 main isomers); boiling point 103°–105° C./40 Pa; $n_D^{20} = 1.4886$.

(b) The procedure described in Example (2a) is repeated, except that 289.5 g (1 mol) of 3-methyl-3-n-propyl-12-(2-pentyl)-1-aza-1,5,9-cyclododecatriene are used. Distillation yields 263 g (0.896 mol) of 3-methyl-3-n-propyl-12-(2-pentyl)-1aza-cyclododecene; boiling point 125° C./53 Pa.

(c) The procedure described in Example (2b) is repeated, except that 293.55 g (1 mol) of 3-methyl-3-n-propyl-12-(2-pentyl)-1-aza-cyclododecene, 82.1 g (0.5 mol) of hydroxylamine sulfate, 100 g of 37% hydrochloric acid, 400 ml of water and 85 g of solid sodium hydroxide are used. The organic phase which separates out contains 325 g (0.996 mol) of 2-methyl-2-n-propyl-11-(2-pentyl)-11-amino-undecanal oxime; yield 99.6% of theory.

EXAMPLE 14

(a) The procedure described in the preceding examples is followed, except that 72.4 g (0.4 mol) of 1-(3-pentyl)-4,4-diethyl-2-aza-1,3-butadiene [prepared by reacting 2-ethylbutyraldehyde with ammonia in accordance with U.S. Pat. No. 2,319,848] and 48.4 g (0.895 mol) of 1,3-butadiene are used. Working up yields 56.8 g (0.197 mol) of 3,3-diethyl -12-(3-pentyl)-1-aza-1,5,9-cyclododecatriene; boiling point 90°–92° C./0.13 Pa; $n_D^{20} = 1.4840$.

(b) The procedure described in Example (2a) is repeated, except that 289 g (1 mol) of 3,3-diethyl-12-(3-pentyl)-1-aza-1,5,9-cyclododecatriene are used. Distillation yields 265 g (0.905 mol) of 3,3-diethyl-12-(3-pentyl)-1-aza-cyclododecene; yield 90.5% of theory; boiling point 95° C./4 Pa.

(c) The procedure described in Example (2b) is repeated, except that 320 g (1.09 mols) of 3,3-diethyl-12-(3-pentyl)-1-aza-cyclododecene, 89.5 g (0.546 mol) of hydroxylamine sulfate, 110 g of 37% hydrochloric acid and 400 ml of water are used. After neutralisation with solid sodium hydroxide, 350 g (1.07 mols) of 2,2-diethyl-11-(3-pentyl)-11-aminoundecanal oxime are obtained; yield 98% of theory; $n_D^{20} = 1.4637$.

EXAMPLE 15

(a) The procedure described in the preceding examples is repeated, except that 760 g (3.21 mols) of N-2-ethylhexylidene-(2-ethyl-hexen-1-yl-amine) [prepared by reacting 2-ethyl-capronaldehyde with ammonia in accordance with U.S. Pat. No. 2,319,848] and 378 g (7 mols) of 1,3-butadiene are used. Working up the reaction mixture yields 930 g (2.69 mols) of 3-ethyl-3-n-butyl-12-(3-heptyl)-1-aza-1,5,9-cyclododecatriene as a 7:3 mixture of the isomers; boiling point 106°–109° C./13 Pa; $n_D^{20} = 1.4895$.

(b) The procedure described in Example (2a) is repeated, except that 396 g (1.15 mols) of 3-n-butyl-3-ethyl-12-(3-heptyl)-1-aza-1,5,9-cyclododecatriene are used. Distillation yields 384 g (1.1 mols) of 3-n-butyl-3-ethyl-12-(3-heptyl)-1-aza-cyclododecene; yield 95.6% of theory; boiling point 130° C./4 Pa.

(c) The procedure described in Example (2b) is repeated, except that 300 g (0.859 mol) of 3-n-butyl-3-ethyl-12-(3-heptyl)-1-aza-cyclododecene, 70.3 g (0.43 mol) of hydroxylamine sulfate and 85 g of 37% hydrochloric acid and also 400 ml of water are used. After neutralisation with solid sodium hydroxide, 329 g (0.86 mol) of 2-n-butyl-2-ethyl-11-(3-heptyl)-11-amino-undecanal oxime are obtained; yield 100% of theory.

EXAMPLE 16

(a) The procedure described in the preceding examples is repeated, except that 467 g (2.8 mols) of N-propylidene-(2-ethyl-hexen-1-yl-amine), 324 g (6 mols) of 1,3-butadiene, 15.7 g (61 mmols) of nickel acetylacetonate, 7.45 g (60 mmols) of trimethyl phosphite, 23.4 g (180 mmols) of ethoxy-diethyl-aluminium and 300 ml of toluene are used. After a reaction time of 4 hours at 40° C., working up yields 624 g (2.27 mols) of 3,12-diethyl-3-n-butyl-1-aza-1,5,9-cyclododecatriene as a mixture of isomers; yield 81% of theory; boiling point 98°–100° C./40 Pa; $n_D^{20} = 1.4905$.

The N-propylidene-(2-ethyl-hexen-1-yl-amine) used in the above example was prepared in a manner analogous to that used for N-propylidene-(2-methylpropenylamine) according to Example (3a), except that 10 g of potassium tert.-butylate, 800 g (4.79 mols) of (2-ethyl-hexylidene)-allylamine and 600 ml of tetrahydrofuran were used. After a reaction time of 2 hours at 35° C., 682 g (4.08 mols) of N-propylidene-(2-ethyl-hexen-1-yl-amine) are obtained; mixture of isomers in a weight ratio of 55:45; boiling point 53°–56° C./133 Pa; $n_D^{20} = 1.4698$.

(b) The procedure described in Example (2a) is repeated, except that 275.5 g (1 mol) of 3-n-butyl-3,12-diethyl-1-aza-1,5,9-cyclododecatriene are used. Distillation yields 245.5 g (0.878 mol) of 3-n-butyl-3,12-diethyl-1-aza-cyclododecene; yield 87.8% of theory; boiling point 110° C./7 Pa.

(c) The procedure described in Example (2b) is repeated, except that 245.5 g (0.878 mol) of 3-n-butyl-3,12-diethyl-1-aza-cyclododecene, 74 g (0.45 mol) of hydroxylamine sulfate, 100 g of 37% hydrochloric acid and 200 ml of water are used. After neutralisation with solid sodium hydroxide, 255 g (0.815 mol) of 2-n-butyl-2,11-diethyl-11-amino-undecanal oxime are obtained; yield 92.9% of theory.

EXAMPLE 17

(a) The procedure described in Example (1a) is repeated, except that 302.5 g (2 mols) of N-cyclohexylidene-(2-methypropenylamine) and 250 g (4.62 mols) of 1,3-butadiene are used. Distillation yields 382 g (1.48 mols) of 3,3-dimethyl-12,12-pentamethylene-1-aza-1,5,9-cyclododecatriene; boiling point 96° C./4 Pa; $n_D^{20} = 1.5116$. The N-cyclohexylidene-(2-methylpropenylamine) was prepared from cyclohexanone and methallylamine, with subsequent isomerisation of the reaction product with potassium tert.-butylate; boiling point 96° C./1,700 Pa; $n_D^{20} = 1.5160$.

(b) The procedure described in Example (1b) is repeated, except that 259.5 g (1 mol) of 3,3-dimethyl-12,12-pentamethylene-1-aza-1,5,9-cyclododecatriene, 69.5 g (1 mol) of hydroxylamine hydrochloride, 20 g of 37% hydrochloric acid and 250 ml of water are used. Working up yields 219.3 g of 2,2-dimethyl-11,11-pentamethylene-11-amino-undeca-4,8-dienal oxime; yield 74.5% of theory; $n_D^{20} = 1.5117$.

EXAMPLE 18

(a) The procedure described in Example (1a) is repeated, except that 94.2 g (0.564 mol) of N-heptylidene-(2-methylpropenylamine) [1-n-hexyl-4,4-dimethyl-2-aza-1,3-butadiene] and 80 g (1.48 mols) of 1,3-butadiene are used. Distillation yields 113 g (0.41 mol) of 3,3-dimethyl-12-n-hexyl-1-aza-1,5,9-cyclododecatriene; boiling point 100° C./4 Pa; $n_D^{20} = 1.4841$.

The N-heptylidene-(2-methylpropenylamine) was heptanal and methallylamine, with subsequent isomerisation of the reaction product with potassium tert.-butylate; boiling point 54° C./5 Pa; $n_D^{20} = 1.4662$.

(b) The procedure described in Example (1b) is repeated, except that 113 g (0.41 mol) of 3,3-dimethyl-12-hexyl-1-aza-1,5,9-cyclododecatriene, 33 g (0.202 mol) of hydroxylamine sulfate, 50 g of concentrated hydrochloric acid and 250 ml of water are used. Working up yields 125 g (0.405 mol) of 2,2-dimethyl-11-n-hexyl-11-amino-undeca-4,8-dienal oxime; yield 99% of theory.

EXAMPLE 19

(a) The procedure described in Example (1a) is repeated, except that 222.4 g (2.0 mols) of N-isopropylidene-(2-methylpropenylamine) are used. Distillation yields 300 g (1.37 mols) of 3,3,12,12-tetramethyl-1-aza- 1,5,9-cyclododecatriene; boiling point 58° C./4 Pa; $n_D^{20}=1.4858$. The N-isopropylidene-(2-methylpropenylamine) was prepared from acetone and methallylamine, with subsequent isomerisation of the reaction product; boiling point 89°–90° C.; $n_D^{20}=1.4762$.

(b) The procedure described in Example (1b) is repeated, except that 110 g (0.5 mol) of 3,3,12,12-tetramethyl-1-aza-1,5,9-cyclododecatriene, 41 g (0.25 mol) of hydroxylamine sulfate, 50 ml of concentrated hydrochloric acid and 250 ml of water are used. Distillation yields 85 g (0.337 mol) of 2,2,11,11-tetramethyl-11-amino-undeca-4,8-dienal oxime; yield 67.4% of theory; boiling point 130° C./7 Pa.

EXAMPLE 20

(a) The procedure described in Example (1a) is repeated, except that 93.6 g (0.5 mol) of N-benzylidene-(2-ethyl-1-butenylamine) [1-phenyl-4,4-diethyl-2-aza-1,3-butadiene, prepared from benzylamine and 2-ethyl-butenal and by subsequent isomerisation of the reaction product in the presence of potassium tert.-butylate; boiling point 70° C./7 Pa; $n_D^{20}=1.5598$; cf. J. Org. Chem., 43, No. 4, 782–84 (1978)] are used. Distillation yields 116 g (0.393 mol) of 3,3-diethyl-12-phenyl-1-aza-1,5,9-cyclododecatriene; boiling point 105° C./4 Pa; $n_D^{20}=1.5369$.

(b) The procedure described in Example (1b) is repeated, except that 95.3 g (0.323 mol) of 3,3-diethyl-12-phenyl-1-aza-1,5,9-cyclododecatriene, 20 g of 37% hydrochloric acid, 22.4 g (0.322 mol) of hydroxylamine hydrochloride and 250 ml of water are used. Working up yields 103.1 g (0.314 mol) of 2,2-diethyl-11-phenyl-11-amino-undeca-4,8-dienal oxime; yield 97.5% of theory.

EXAMPLE 21

(a) The procedure described in Example (1a) is repeated, except that 215.3 g (1 mol) of N-benzylidene-(2-ethyl-1-hexenylamine) [1-phenyl-4-ethyl-4-n-butyl-2-aza-1,3-butadiene; prepared by reacting benzylamine with 2-ethyl-hexenal and then isomerising the reaction product with potassium tert.-butylate; boiling point 90° C./7 Pa; $n_D^{20}=1.5630$] are used. Distillation yields 288 g (0.891 mol) of 3-n-butyl-3-ethyl-12-phenyl-1-aza-1,5,9-cyclododecatriene; boiling point 130° C./2 Pa; $n_D^{20}=1.5296$.

(b) The procedure described in Example (1b) is repeated, except that 283.4 g (0.875 mol) of 3-n-butyl-3-ethyl-12-phenyl-1-aza-1,5,9-cyclododecatriene, 60.8 g (0.87 mol) of hydroxylamine hydrochloride, 50 ml of concentrated hydrochloric acid and 250 ml of water are used. Working up yields 310 g (0.87 mol) of 2-n-butyl-2-ethyl-11-phenyl-11-amino-undeca-4,8-dienal oxime; yield 99.5% of theory.

EXAMPLE 22

(a) The procedure described in Example (1a) is repeated, except that 184 g (1.34 mols) of N-(2-ethyl)-buten-2-ylidene-propenylamine [prepared by reacting 2-ethyl-butenal and allylamine and subsequently isomerising the reaction product, analogously to Zhurnal Organicheskoi Khimii, 6, No. 2197–9 (1970); boiling point 70° C./1,700 Pa; $n_D^{20}=1.5227$] are used. Distillation yields 295 g (1.21 mols) of 3-methyl-12-(3-penten-2-yl)-1-aza-1,5,9-cyclododecatriene; boiling point 100° C./4 Pa; $n_D^{20}=1.5056$.

(b) The procedure described in Example (1b) is repeated, except that 122.7 g (0.5 mol) of 3-methyl-12-(3-penten-2-yl)-1-aza-1,5,9-cyclododecatriene, 41.1 g (0.25 mol) of hydroxylamine sulfate, 50 ml of concentrated hydrochloric acid and 250 ml of water are used. Working up yields 135.9 g (0.488 mol) of 2-methyl-11-(3-penten-2-yl)-11-amino-undeca-4,8-dienal oxime; yield 97.6% of theory. $n_D^{20}=1.5091$.

EXAMPLE 23

(a) The procedure described in Example (1a) is repeated, except that 105 g (0.765 mol) of N-(2-ethyl)-buten-2-ylidene-propenylamine and 120 g (1.76 mmols) of isoprene are used. After a reaction time of 5 hours at 90° C., subsequent distillation yields 85 g (0.312 mol) of 3,5(or 6),9(or 10)-trimethyl-12-(3-penten-2-yl)-1-aza-1,5,9-cyclododecatriene; boiling point 108°–110° C./5 Pa; $n_D^{20}=1.5078$.

(b) The procedure described in Example 1(b) is repeated, except that 83.75 g. (0.305 mol) of the above 1-aza-1,5,9-cyclododecatriene, 26.8 g (0.163 mol) of hydroxylamine sulfate, 35 ml of concentrated hydrochloric acid and 250 ml of water are used. Working up yields 90 g (0.294 mol) of 2,4(5), 8(9)-trimethyl-11-(3-penten-2-yl)-11-aminoundeca-4,8-dienal oxime; yield 96.5% of theory.

EXAMPLE 24:

The procedure described in Example 1(b) is repeated, except that 23.3 g (0.1 mol) of 3,3-dimethyl-12-isopropyl-1-aza-1,5,9-cyclododecatriene, 20 g of 37% hydrochloric acid, 20 ml of water and 10.8 g (0.1 mol) of phenylhydrazine are used. Working up as described in Example 1(b) yields 34.1 g (0.1 mol) of 2,2-dimethyl-11-isopropyl-11-amino-undeca-4,8-dienal phenylhydrazone; yield 100% of theory.

Analysis for $C_{22}H_{35}N_3$ (molecular weight 341.54): calculated C: 77.37%; H: 10.33%; N: 12.30%; found C: 77.03%; H: 10.58%; N: 12.23%.

Mass spectrum: molecule peak 341, fragment masses 298, 270, 234, 161, 92 and 72.

$^1$H-NMR spectrum $\tau$(ppm): 2.65–3.3(m), 4.58(m), 7.45 (dt) 7.89(m), 8.03(s), 8.35(m), 8.88(s) and 9.06(dd) in a ratio of 7:4:1:8:1:6:6.

EXAMPLE 25:

The procedure described in Example 1(b) is repeated, except that 46.6 g (0.2 mol) of 3,3-dimethyl-12-isopropyl-1-aza-1,5,9-cyclododecatriene, 40 g of 37% hydrochloric acid, 40 ml of water and 5 g (0.1 mol) of hydrazine hydrate are used. Working up yields 42 g (0.84 mol) of di-(2,2-dimethyl-11-isopropyl-11-amino-undeca-4,8-dienal) hydrazone; yield 84% of theory.

Analysis for $C_{32}H_{58}N_4$ (molecular weight 498.84): calculated C: 77.05%; H: 11.72%; N: 11.23%; found C: 77.83%; H: 12.08%; N: 10.84%. Mass spectrum: molecule peak 498, fragment masses 483, 455, 438, 426, 372, 318 and 276.

$^1$H-NMR spectrum $\tau$(ppm): 2.38 (s), 4.58(m), 7.5(m), 7.88(m), 8.1–8.7(m), 8.88(s) and 9.06 (dd) in a ratio of 2:8:2:16:6:12:12.

EXAMPLE 26:

The procedure described in Example 1(b) is repeated, except that 23.3 g (0.1 mol) of 3,3-dimethyl-12-isopropyl-1-aza-1,5,9-cyclododecatriene, 20 g of 37% hydrochloric acid, 20 ml of water and 11.15 g (0.1 mol) of semicarbazide hydrochloride are used. Working up yields 26.5 g (0.086 mol) of 2,2-dimethyl-11-isopropyl- 11-amino-undeca-4,8-dienal semicarbazone; yield 86% of theory.

Analysis for $C_{17}H_{32}N_4O$ (molecular weight 308.47): calculated C: 66.19%; H: 10.46%; N: 18.16%; O: 5.19%; found C: 68.5%; H: 10.5%; N: 17.4%; O: 5.0%.

Mass spectrum: molecule peak 308, fragment masses 265, 248, 205, 182, 129 and 72.

$^1$H-NMR spectrum $\tau$(ppm): 0.9(m), 2.98(s), 4.32(s), 4.58(m), 7.48(dt), 7.9(m), 8.1–8.8(m), 8.91(s) and 9.06(dd) in a ratio of 1:1:2:4:1:8:3:6:6.

EXAMPLE 27:

The procedure described in Example 2(b) is repeated, except that 68.5 g (0.5 mol) of 3,3-dimethyl-12-isopropyl-1-aza-cyclododecene, 50 g of 37% hydrochloric acid, 54 g (0.5 mol) of benzylamine and 200 ml of water are used. After neutralisation with 22 g (0.55 mol) of solid sodium hydroxide, 97 g (0.282 mol) of 2,2-dimethyl-11-isopropyl-11-amino-undecanal-benzylamine are obtained; yield 56.4% of theory.

Analysis for $C_{23}H_{40}N_2$ (molecular weight 344.59): calculated C: 80.17%; H: 11.70%; N: 8.13%, found C: 80.0%; H: 12.1%; N: 7.7%.

Mass spectrum: molecule peak 344, fragment masses 301, 253, 161 and 91.

$^1$H-NMR spectrum $\tau$(ppm): 2.7(m), 6.18(s) and 7.3–9.2(m) in a ratio of 6:2:32.

Conversion to diamines of the formula VIII:

490 g (1.84 moles) of the 2,2-dimethyl-11-isopropyl-11-amino-undeca-4,8-dienal oxime obtained according to Example 5 are dissolved in 2.4 liters of methanol and this solution is filled, together with about 200 g of liquid ammonia, with the addition of 150 g of Raney nickel, into a 6.3 liter steel autoclave. Hydrogen is then injected until the pressure is 100 bars and the mixture is heated to 100° C. with stirring. The mixture is hydrogenated for about 5 hours under these conditions and cooled and the ammonia and excess hydrogen are then allowed to blow off. Subsequent distillation under a high vacuum yields 436 g (1.705 mols) of 1-isopropyl-10,10-dimethyl-1,11-diaminoundecane in the form of a colourless, water-clear liquid; boiling point 87° C./4 Pa; $n_D^{20} = 1.4619$.

The 2,2-dimethyl-11-isopropyl-11-amino-undecanal oxime prepared according to Example 7 can be hydrogenated to 1-isopropyl-10,10-dimethyl-1,11-diaminoundecane in an analogous manner.

When the above example is repeated using, in place of 2,2-dimethyl-11-isopropyl-11-amino-undeca-4,8-dienal oxime, 34.1 g (0.1 mol) of 2,2-dimethyl-11-isopropyl-11-amino-undeca-4,8-dienal phenylhydrazine (prepared according to Example 24), 42 g (0.084 mol) of di-(2,2-dimethyl-11-isopropyl-11-amino-undeca-4,8-dienal) hydrazone (prepared according to Example 25), 26.5 g (0.086 mol) of 2,2-dimethyl-11-isopropyl-11-amino-undeca-4,8-dienal semicarbazone (prepared according to Example 26) or . . . 2,2-dimethyl-11-isopropyl-11-amino-undecanal-benzylamine (prepared according to Example 27), 1-isopropyl-10,10-dimethyl-1,11-diaminoundecane is obtained in a yield of 76% of theory, 60.6% of theory, 62.6% of theory and 72% of theory respectively.

The following diamines were prepared in the manner described above: 1-methyl-10-phenyl-1,11-diaminoundecane; boiling point 138°–140° C./1 Pa; $n_D^{20} = 1.5095$ (oxime according to Example 1 or 2); 1-ethyl-10,10-dimethyl-1,11-diaminoundecane; boiling point 93° C./7 Pa; $n_D^{20} = 1.4622$ (oxime according to Example 3 or 4); 1,1,10-trimethyl-1,11-diaminoundecane; boiling point 87° C./4 Pa; $n_D^{20} = 1.4585$ (oxime according to Example 8); 1-cyclohexyl-10-pentamethylene-1,11-diaminoundecane; boiling point 166°–170° C./3 Pa; $n_D^{20} = 1.4975$ (oxime according to Example 9); 1-phenyl-10,10-dimethyl-1,11-diaminoundecane; boiling point 150° C./3 Pa; $n_D^{20} = 1.5054$ (oxime according to Example 10); 1-(2-furyl)-10-methyl-1,11-diaminoundecane; boiling point 135°–138° C./7 Pa; $n_D^{20} = 1.4869$ (oxime according to Example 11); 1-cyclopentyl-10-tetramethylene-1,11-diaminoundecane; boiling point 166°–168° C./5 Pa; $n_D^{20} = 1.4922$ (oxime according to Example 12); 1(2-pentyl)-10-methyl-10-n-propyl-1,11-diaminoundecane; 140°–142° C./3 Pa; $n_D^{20} = 1.4665$ (oxime according to Example 13); 1-(3-pentyl)-10,10-diethyl-1,11-diaminoundecane; boiling point 133°–135° C./3 Pa; $n_D^{20} = 1.4704$ (oxime according to Example 14); 1-(3-heptyl)-10-n-butyl-10-ethyl-1,11-diaminoundecane; boiling point 156°–160° C./4 Pa; $n_D^{20} = 1.4672$ (oxime according to Example 15); 1,10-diethyl-10-n-butyl-1,11-diaminoundecane; boiling point 128°–130° C./5 Pa; $n_D^{20} = 1.4630$ (oxime according to Example 16); 1-pentamethylene-10,10-diethyl-1,11-diaminoundecane; boiling point 112° C./4 Pa; $n_D^{20} = 1.4833$ (oxime according to Example 17); 1-n-hexyl-10,10-dimethyl-1,11-diaminoundecane; boiling point 135° C./4 Pa; $n_D^{20} = 1.4624$; 1,1,10,10-tetramethyl-1,11-diaminoundecane; boiling point 92° C./5 Pa; $n_D^{20} = 1.4590$; 1-phenyl-10,10-diethyl-1,11-diaminoundecane; boiling point 146° C./2 Pa; $n_D^{20} = 1.5090$; 1-phenyl-10-n-butyl-10-ethyl-1,11-diaminoundecane; boiling point 155°–158° C./5 Pa; $n_D^{20} = 1.5045$; 1-(3-pentyl)-10-methyl-1,11-diaminoundecane; boiling point 115° C./5 Pa; $n_D^{20} = 1.4662$; and (1-(3-pentyl)-3(4),7(8),10-trimethyl-1,11-diaminoundecane; boiling point 117° C./2 Pa; $n_D^{20} = 1.4731$.

USE EXAMPLES

EXAMPLE A:

54.5 g of terephthalic acid are suspended in a mixture of 750 ml of ethanol and 750 ml of water, in a flask which is provided with a stirrer, a dropping funnel and a reflux condenser, and the suspension is refluxed. 103.2 g of 1-(3-pentyl)-10,10-diethyl-1,11-diaminoundecane are then added to the suspension from the dropping funnel. After 20 minutes, the mixture is slowly cooled to room temperature (20°–25° C.) and the salt which has precipitated out is filtered off. After drying in vacuo, 147 g (93% of theory) of the salt are obtained. 10 g of this salt are sealed under nitrogen in a bomb tube and heated for one hour at 270° C. in a salt bath. During this time, the salt melts to give a colourless melt. After cooling to room temperature, the solidified melt is removed from the bomb tube and kept in an open polycondensation apparatus for 6 hours at 270° C., with the exclusion of air and whilst continuously passing nitrogen through the apparatus. On cooling, the viscous melt solidifies to a glass-clear, colourless mass. The reduced solution viscosity of the resulting polyamide, measured on a 0.5% solution in m-cresol at 25° C., is 0.91 dl/g; glass transition temperature, determined in a differential calorimeter (DSC), = 123° C.

A film produced at 270° C. by means of a hydraulic press is exposed, at room temperature, to a relative atmospheric humidity of 65% until no further increase in weight is observed. The saturation value is 0.7 per cent by weight. If the film is exposed to the action of boiling water, no impairment whatsoever in the transparency can be observed even after 6 hours.

EXAMPLE B:

0.1 mol of terephthalic acid in 300 ml of 70% ethanol are heated to the boil in a round-bottomed flask, which is provided with a stirrer, a reflux condenser and a dropping funnel. 0.1 mol of 1-cyclohexyl-10-pentamethylene-1,11-diaminoundecane is allowed to run from the dropping funnel into the boiling suspension in the course of about 10 minutes, with stirring, and residues of diamine adhering to the dropping funnel are rinsed quantitatively into the reaction mixture using a little ethanol. The resulting clear solution is allowed to cool, with continuous stirring, and the salt which has precipitated is filtered off and dried in vacuo at 90° C.

The following components are weighed into a bomb tube, which is provided with a screw top fitted with a pressure relief of valve: 2.156 g of 4,4'-diamino-3,3'-dimethyldicyclohexylmethane, 1.502 g of isophthalic acid and 8.535 g of the salt obtained from 1-cyclohexyl-10-pentamethylene-1,11-diaminoundecane and terephthalic acid.

After the air in the bomb tube has been completely displaced by nitrogen, the bomb tube is closed and immersed in a salt bath, the temperature of which is 270° C. After 30–60 minutes, a homogeneous, glass-clear melt has formed. After a total of 3 hours, the pre-condensation is discontinued by removing the bomb tube from the salt bath and releasing the excess pressure by opening the valve. The solidified, glass-clear precondensate is removed from the bomb tube and transferred to a condensation vessel. With strict exclusion of air and whilst continuously passing nitrogen through the vessel, the melt is subjected to polycondensation at a salt bath temperature of 280° C. for 5 hours, the water of reaction being removed continuously by the stream of nitrogen. On cooling, the melt solidifies to a glass-clear mass.

2–3 g of the copolyamide prepared are pressed in a heatable hydraulic press at 270° C. to give a film about 0.4 mm to 1 mm thick. In order to determine the absorption of water, the film is exposed, at room temperature, to a relative atmospheric humidity of 65% until no further increase in weight is observed. The saturation value is 1.2 percent by weight. The reduced solution viscosity of the copolyamide, measured on a 0.5% solution in m-cresol at 25° C., is 1.09 dl/g; glass transition temperature, determined in a differential calorimeter (DSC),=166° C. The stability of the transparency towards boiling water is very good, i.e. no impairment in the transparency of the copolyamide is detectable even after several days.

EXAMPLE C:

34 g of 1-isopropyl-10,10-dimethyl-1,11-diaminoundecane and 2 g of 2,4,6-tris-(dimethylamino-methyl)-phenol are mixed at room temperature with 100 g of a liquid polyglycidyl ether, which has been prepared by a condensation reaction of bisphenol A with epichlorohydrin in the presence of alkali and has an epoxide content of 5.3 epoxide equivalents/kg and a viscosity of 8,000–12,000 mPa.s at 25° C.

This mixture is applied as a lacquer. The following properties are measured, both on the curable mixture, which is distinguished by an advantageously long pot life, and on the cured lacquer:

| | |
|---|---|
| viscosity according to DIN*) 53,015 [mPa.s] | = 600 |
| gel time (Tecan apparatus) [hours] | = 11.15 |
| dust-dry time; film thickness 200 μm (type 338 drying time testing apparatus from Erichson) [hours] | = 30 |
| time for complete cure (drying time testing apparatus as above) [hours] | = >30 |
| Persoz hardness; film thickness 200 μm; after storing for 1 week at 20° C. [seconds] | = 350 |
| Erichsen test**) (DIN 53,156); film thickness 200 μm; | |
| after storing for 1 week at 20° C. [mm] | = 3.0 |
| after storing for 1 week at 60° C. [mm] | = 6.0 |
| Impact test; film thickness 200 μm; | |
| after storing for 1 week at 20° C. [cm kg] | = 60 |
| after storing for 1 week at 60° C. [cm kg] | = 90 |
| mandrel bending test (DIN 53,152); film thickness 200 μm; mandrel 15 mm | |
| after storing for 1 week at 20° C. [degrees] | = 10 |
| after storing for 1 week at 60° C. [degrees] | = 180 |

*)DIN = Deutsche Industrie-Norm
**)The test is carried out at 20° C./65% atmospheric humidity. Impact is on the film, weight of the test hammer: 1 kg, diameter of the impacting hemisphere: 2 cm.

What is claimed is:

1. A compound of formula Ia

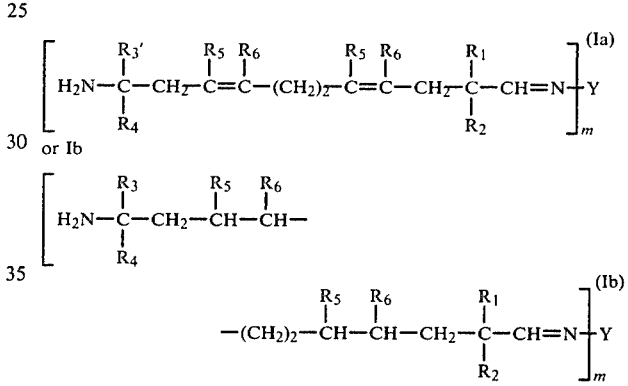

or Ib in which m is the number 1, Y is OH or NH$_2$, R$_1$ is alkyl having 1–12 C atoms, R$_2$ is hydrogen or alkyl having 1–12 C atoms, R$_3$ is alkyl having 1–12 C atoms, cycloalkyl having 4–12 ring C atoms, aralkyl having 7 or 8 C atoms, phenyl, 1-naphthyl, 2-naphthyl, or said phenyl or said naphthyl substituted by alkyl having 1–4 C atoms, R$_3$' has the meaning defined for R$_3$ or, if R$_4$ is hydrogen, is also —C=CH-alkyl or —C(alkyl)=CH-alkyl, each having 1–4 C atoms in the alkyl moiety, and R$_4$ is hydrogen alkyl having 1–12 C atoms, cycloalkyl having 4–12 ring C atoms, aralkyl having 7 or 8 C atoms, phenyl, 1-naphthyl, 2-naphthyl, or said phenyl or said naphthyl substituted by alkyl having 1–4 C atoms, or R$_1$ and R$_2$, R$_3$ and R$_4$ or R$_3$' and R$_4$; or both R$_1$ and R$_2$; and R$_3$ and R$_4$; or both R$_1$ and R$_2$; and R$_3$' and R$_4$, together are alkylene having 3–11 C atoms, and R$_5$ and R$_6$ independently of one another are hydrogen or methyl.

2. A compound of the formula Ia or Ib according to claim 1, in which R$_1$ is alkyl having 1–5 C atoms and R$_2$ is hydrogen or alkyl having 1–5 C atoms, or R$_1$ and R$_2$ together are alkylene having 4–7 C atoms, R$_3$ is alkyl having 1–7 C atoms, cycloalkyl having 5–8 C atoms or unsubstituted phenyl, R$_3$' has the meaning defined for R$_3$ or, if R$_4$=H, is also —C(C$_2$H$_5$)=CH—CH$_3$, R$_4$ is hydrogen or alkyl having 1–5 C atoms and R$_5$ and R$_6$ are each hydrogen.

3. A compound of the formula Ia or Ib according to claim 1, in which m is the number 1, Y is —OH, R$_1$ is alkyl having 1–5 C atoms and $R_2$ is alkyl having 1–5 C atoms or hydrogen, or $R_1$ and $R_2$ together are alkylene having 4–7 C atoms, $R_3$ is branched alkyl having 3–7 C atoms or cycloalkyl having 5–8 C atoms, $R_3'$ has the meaning defined for $R_3$ or is $-C(C_2H_5)=CH-CH_3$ and $R_4$, $R_5$ and $R_6$ are each hydrogen.

4. A compound of the formula Ia or Ib according to claim 1, in which m is the number 1, Y is $-OH$, $R_1$ and $R_2$ are each methyl or ethyl or together are $C_{4-7}$-alkylene, $R_3$ or $R_3'$ are isopropyl, 3-pentyl or $C_{5-8}$-cycloalkyl, and $R_4$, $R_5$ and $R_6$ are each hydrogen.

5. A compound as claimed in claim 1 having the formula

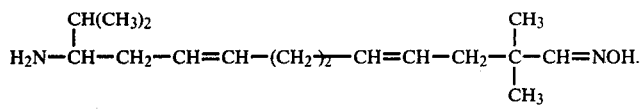

6. A compound as claimed in claim 1 having the formula

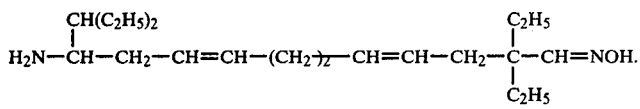

7. A compound as claimed in claim 1 having the formula

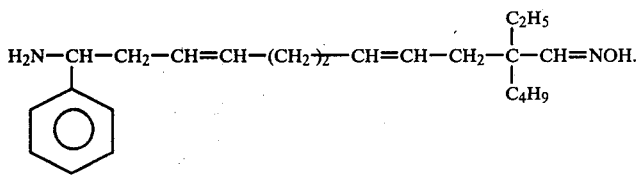

8. A compound according to claim 4 wherein $R_1$ and $R_2$ together are pentamethylene.

9. A compound according to claim 4 wherein $R_3$ and $R_3'$ is cyclohexyl.

* * * * *